(12) United States Patent
Bajwa

(10) Patent No.: US 9,671,208 B2
(45) Date of Patent: Jun. 6, 2017

(54) SUPPLY OF PILLOWS, AND A DEVICE FOR USE THEREIN

(76) Inventor: Kulwinder Bajwa, Great Missenden (GB)

( * ) Notice: Subject to any disclaimer, the term of this patent is extended or adjusted under 35 U.S.C. 154(b) by 0 days.

(21) Appl. No.: 13/983,485

(22) PCT Filed: Feb. 14, 2012

(86) PCT No.: PCT/GB2012/000152
§ 371 (c)(1),
(2), (4) Date: Aug. 2, 2013

(87) PCT Pub. No.: WO2012/110761
PCT Pub. Date: Aug. 23, 2012

(65) Prior Publication Data
US 2013/0298334 A1    Nov. 14, 2013

(30) Foreign Application Priority Data

Feb. 15, 2011   (GB) .................................. 1102626.7
Mar. 29, 2011   (GB) .................................. 1105219.8

(51) Int. Cl.
*A47G 9/10*      (2006.01)
*G01B 3/20*      (2006.01)
*A61B 5/107*      (2006.01)

(52) U.S. Cl.
CPC ................. *G01B 3/20* (2013.01); *A47G 9/10* (2013.01); *A61B 5/1072* (2013.01); *G01N 2203/0085* (2013.01); *G01N 2203/0246* (2013.01)

(58) Field of Classification Search
CPC ...................................................... A47G 9/10
(Continued)

(56) References Cited

U.S. PATENT DOCUMENTS 4,140,008 A    2/1979   Golembeck et al.
5,351,408 A   10/1994   Street
(Continued)

FOREIGN PATENT DOCUMENTS

CN     201255617 Y    6/2009
DE       9307681 U1    8/1993
(Continued)

OTHER PUBLICATIONS

International Search Report and Written Opinion; PCT/GB2012/000152; Jul. 20, 2012.
(Continued)

*Primary Examiner* — Fredrick Conley
(74) *Attorney, Agent, or Firm* — Westman, Champlin & Koehler, P.A.; Z. Peter Sawicki; A. Prose

(57) ABSTRACT

An improvement in the process of pillow selection is described, allowing customers to select a pillow that is appropriate for them in a less random manner. First, a method of selecting a pillow for a user is disclosed, comprising the steps of locating the user with a shoulder thereof adjacent a flat rigid surface, orienting the user substantially transverse to the surface, measuring a spacing between the surface and a proximate side of the user's head, and selecting at least one pillow from a group of pillows, based on the measured spacing. The rigid surface is ideally upright, such as a wall. The group of pillows can be divided into a plurality of sub-groups, each sub-group containing a plurality of pillows with substantially like thickness. Thus, based on the reading, the user can be invited to choose any pillow from a specific group or range of pillows. Second, an apparatus for assisting in the selection of a pillow is disclosed, comprising an extending center section located between a pair of opposing end plates, the center section having a visible indicia indicative of a distance between the (Continued)

end plates. The center section is ideally telescopic, and can comprise an inner and an outer telescopic sleeve, the visible indicia then being provided on the inner telescopic sleeve. A series of colored bands as the visible indicia allows the relevant group of pillows to be identified easily, quickly and unambiguously.

8 Claims, 3 Drawing Sheets

(58) Field of Classification Search
USPC .................. 5/630, 636, 640; 33/511, 512
See application file for complete search history.

(56) References Cited

U.S. PATENT DOCUMENTS

| | | | |
|---|---|---|---|
| 5,457,832 A | 10/1995 | Tatum | |
| 5,873,175 A * | 2/1999 | Johnston | 33/809 |
| 5,974,678 A | 11/1999 | Landauer | |
| 6,676,069 B1 | 1/2004 | Davis | |
| 7,841,098 B2 * | 11/2010 | Richter | 33/512 |
| 2005/0150124 A1 | 7/2005 | Greenawalt et al. | |
| 2010/0192395 A1 * | 8/2010 | MacFarlane | 33/512 |

FOREIGN PATENT DOCUMENTS

| | | |
|---|---|---|
| DE | 4411609 A1 | 8/1994 |
| DE | 202006019485 U1 | 3/2007 |
| EP | 1845354 A2 | 10/2007 |
| FR | 2907771 A1 | 5/2008 |
| GB | 1169514 A | 11/1969 |
| GB | 2407031 A | 4/2005 |
| JP | 10168631 A | 6/1998 |
| JP | 2001299545 A | 10/2001 |
| JP | 2004209099 A | 7/2004 |
| JP | 2005245572 A | 9/2005 |
| JP | 2009183412 A | 8/2009 |
| WO | 02103281 A1 | 12/2002 |
| WO | 2006096808 A2 | 9/2006 |
| WO | 2006125250 A1 | 11/2006 |

OTHER PUBLICATIONS

GB Search Report; GB1105219.8; Jul. 15, 2011.
GB Search Report; GB1102626.7; Jun. 10, 2011.
GB Search Report; GB1102626.7; Aug. 19, 2011.

* cited by examiner

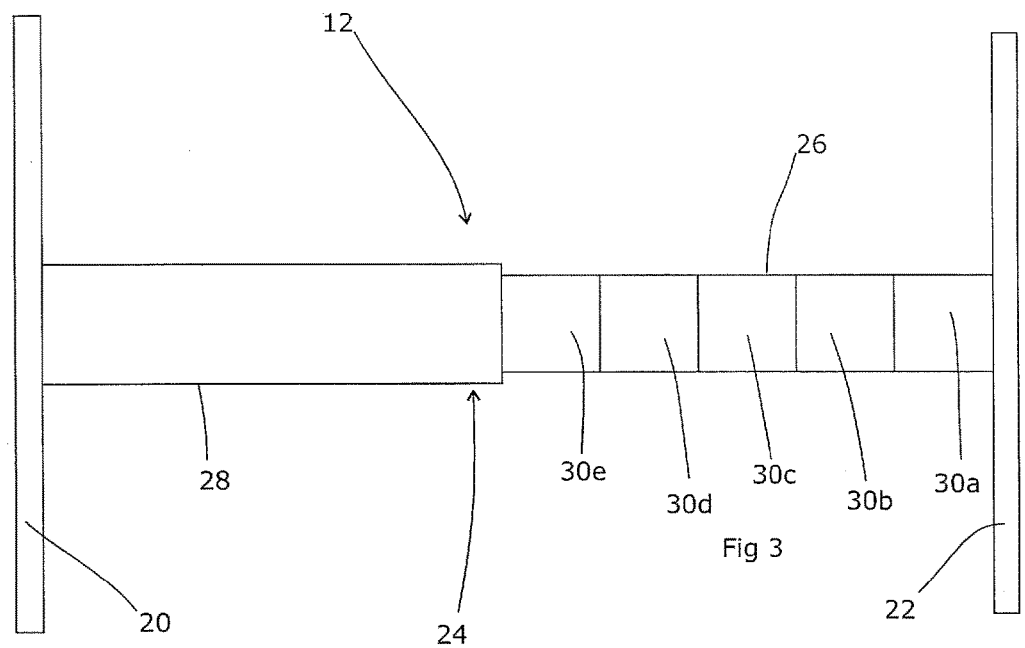
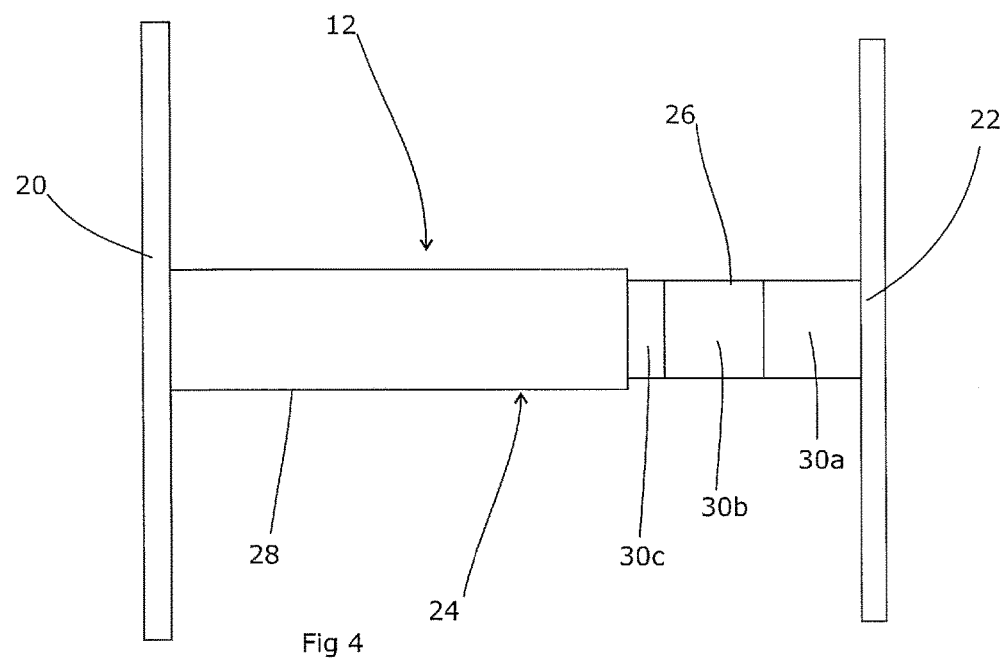

SUPPLY OF PILLOWS, AND A DEVICE FOR USE THEREIN

CROSS-REFERENCE TO RELATED APPLICATIONS

This application is a Section 371 National Stage Application of International Application No. PCT/GB2012/000152, filed Feb. 14, 2012, and published as WO 2012/110761, on Aug. 23, 2012, in English, which claims priority to and benefits of GB Application No. 1102626.7, filed Feb. 15, 2011, and GB Application No. 1105219.8, filed Mar. 29, 2011, the contents of which are hereby incorporated by reference in their entirety.

FIELD OF THE INVENTION

The present invention relates to pillows, and sets out a method for the selection of an appropriate pillow and apparatus for use therein.

BACKGROUND ART

A pillow is an essential part of healthy sleep. By "pillow", we mean a support for the head, usable while sleeping in a bed. In most cases, pillows are cushioned, i.e. padded and therefore compliant to some degree, with a varying degree of softness, but this is not universally the case.

Internally, most pillows comprise a filler made from foam, synthetic fills, feathers, down, buckwheat (and polymeric imitations), cotton, air, or a suitable fluid. The fill is surrounded with a cover or shell made of cloth or silk, known as the pillow case or pillow slip.

Pillows can be used to provide support for the head while sleeping, to prevent the head from drooping. If such support is not provided, then neck and head discomfort can result and sleep can be disturbed. Both will have undesirable effects on the sufferer.

SUMMARY OF THE INVENTION

The present invention addresses the need to provide not only support, but also an appropriate level of support. Generally, most people choose a pillow based on aesthetic qualities, degree of compliance, and brand. Once purchased, pillows will then be regarded as either "comfortable" or "uncomfortable" by the owner, seemingly at random. Often, a customer with sleeping difficulties will try several pillows before finding one that is "comfortable" and which gives an acceptable night's sleep. Whilst this repeated purchasing is beneficial for the pillow suppliers, it is wasteful of the customer's time and money, and unnecessarily prolongs the period of poor sleeping. It is therefore inefficient.

The present invention therefore seeks to improve upon the process of pillow selection, allowing customers to select a pillow that is appropriate for them in a less random manner. In its first aspect, the invention therefore provides a method of selecting a pillow for a user, comprising the steps of locating the user with a shoulder thereof adjacent an upright flat rigid surface, orienting the user substantially transverse to the surface, measuring a spacing between the surface and a proximate side of the user's head, and selecting at least one pillow from a group of pillows, based on the measured spacing.

The upright nature of the surface makes the process more comfortable and convenient for the user. This avoids the need to recline the user, and limits the amount of space necessary to take the measurement thereby making it feasible for use in a wide range of retail establishments. A wall provides a convenient surface.

The method of the invention can use an apparatus as defined below (in relation to the second aspect) to determine the necessary measurement. Alternatively, a time-of-flight device such as a laser measuring device or an ultrasonic measuring device can be used. These devices send a pulse of light, sound, or other travelling wave which is reflected off the head, the wall, or other adjacent surface and the time of flight of the travelling wave is measured. Combined with prior knowledge of the speed of the travelling wave, this yields the distance. It is also possible to use a linear scale such as a ruler or callipers, but these are usually less convenient.

The group of pillows can be divided into a plurality of sub-groups, each sub-group containing a plurality of pillows with substantially like thickness. Thus, based on the reading, the user can be invited to choose any pillow from a specific group or range of pillows. The pillows preferably carry a visible indicia indicating the sub-group to which they each belong. This indicia can match the coloured or numeric marking on bands provided on the telescopic measuring apparatus.

In a second aspect, the invention relates to an item of apparatus for assisting in the selection of a pillow. Such an item allows the deltoid temporal distance (i.e. the distance between the outer extremity of the shoulder muscle and the temporal bone) to be measured with ease, which we have found to be important in determining the correct pillow for the person concerned.

The item comprises an extending centre section located between a pair of opposing end plates, the centre section having a visible indicia indicative of a distance between the end plates. The centre section is ideally telescopic, and can comprise an inner and an outer telescopic sleeve, the visible indicia then being provided on the inner telescopic sleeve. A series of coloured or numbered bands as the visible indicia allows the relevant group of pillows to be identified easily, quickly and unambiguously.

The end plates of the device are preferably flat, but can be suitably contoured if preferred. The can be wider than the diameter or thickness of the centre section, thereby providing the operator with an easy means of manipulation. Alternatively, they can simply be end caps of the centre section.

It is possible to design the device such that one end plate has a dimension transverse to the centre section that is greater than that of the other end plate. In this way, the end plate can provide a flat rigid surface to abut against the outside of the shoulder, and measurements can be carried out anywhere. Alternatively, the person can stand adjacent a wall, for the device to measure the gap between the side of the head and the wall and this determine the deltoid temporal distance.

In a third aspect, the present invention provides a method of quantifying the thickness of a pillow according to a scale that can be reliable and consistent. Thus, the present invention provides a method of measuring a linear dimension of a pillow, comprising the steps of applying a predetermined compressive force to at least part of the pillow and measuring the thickness of the thus compressed pillow. The compressive force is preferably applied between a pair of jaws, one of which can be static and one of which can be moveable thereby to apply the force. One of the jaws can be resiliently deformable, in the manner of a mattress. The thickness of the compressed pillow can be measured by determining the spacing of the jaws after application of the force. A proximity sensor can be used in order to do so, if desired.

According to the third aspect, a corresponding apparatus is provided. Such apparatus could comprise a first planar surface and a second planar surface between which a pillow is placeable, a means for exerting a compressive force between the two surfaces, and a means for determining the spacing between the surfaces. A ballast weight is a convenient means for exerting the compressive force.

BRIEF DESCRIPTION OF THE DRAWINGS

An embodiment of the present invention will now be described by way of example, with reference to the accompanying figures in which;

FIG. 3 shows a side view of the pillow selection tool in an extended state;

FIG. 4 shows a side view of the pillow selection tool, in a compressed state.

DETAILED DESCRIPTION OF THE EMBODIMENTS

The present invention seeks to make efficiencies in the selection and supply of pillows, by making it possible to match a pillow to its intended recipient. As described above, this is mainly done on a relatively random basis in that the need to match a pillow to a user is insufficiently appreciated, and the means to measure a user with accuracy is absent. In a nutshell, currently there is no standardisation of pillows and generally one does not know what height pillow is right for any individual. Pillows are usually bought on the basis of feel and/or trial and error.

About 70% of the population sleeps on their side. The function of a pillow is primarily to support the head and allow correct alignment of the body, and in particular the spine, when one is lying down. By accurately measuring the individual, in particular the deltoid temporal distance, the correct pillow size can be advised.

Thus, the overall concept is to:
1. Standardise pillow heights into different sizes or size groups,
2. Measure individuals to identify their correct pillow size, based on their deltoid temporal distance,
3. Dispense a pillow suited to the individual in question.

Figure 1:
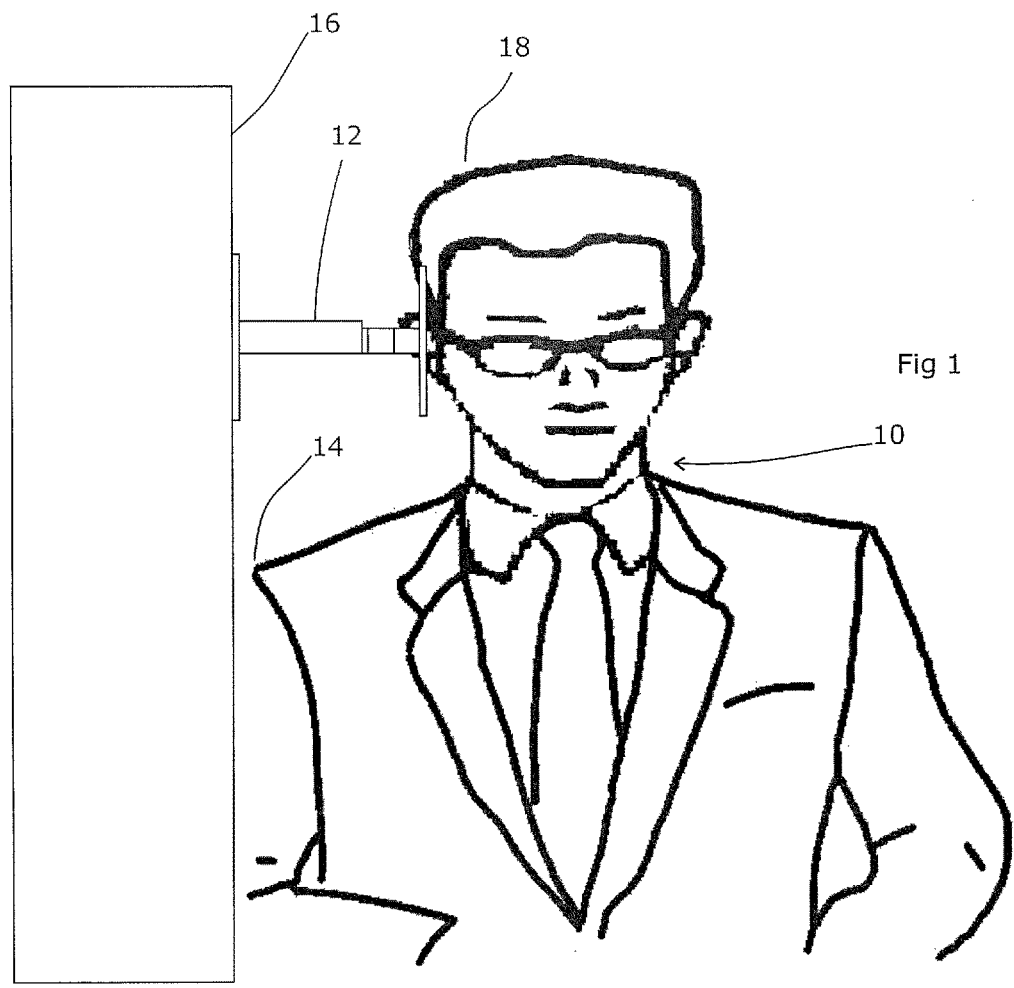
FIG. 1 shows a user being measured for a pillow according to the present invention.

As mentioned above, this requires that there be an adequate way of measuring an individual's correct pillow size. FIGS. 1 to 4 show the pillow sizer of the present invention, and how it can be used to measure an individual for their correct pillow size. As shown in FIG. 1, the pillow sizer measures the distance between the outer part of an individual's shoulder and their head. This is, in practice, the distance between the outer part of the deltoid muscle and the temporal bone, i.e. the deltoid-temporal distance. The individual 10 is measured while standing up or sitting facing forward, with their shoulder 14 abutting a smooth vertical surface such as a wall 16, standing transverse to the wall 16. The pillow sizer 12 measures the distance between the wall 16 and the near side of individual's head 18 the measurement taken (A) corresponds to a particular standardised pillow size.

This yields an ideal thickness for the pillow. A pillow which, in use, adopts this thickness will support the individual's head when they lie on their side such that the head is in line with the spine and (hence) the spine and neck are horizontal. This avoids imposing a strain or deformation on the spine and/or neck, both of which are associated with discomfort and poor sleep. The standardised pillows are then dispensed according to the size required.

Pillows are of course soft, to varying degrees, and therefore compress when a head is placed on them. Therefore, it is the thickness when compressed which is particularly relevant. Generally, this is related to the thickness when uncompressed, in that the mass or weight of a head scales with the measured shoulder dimension. Thus, a single size group may include a relatively softer but thicker pillow and a relatively firmer but thinner pillow, both of which compress under the weight of a head to approximately the same thickness.

Figure 2:
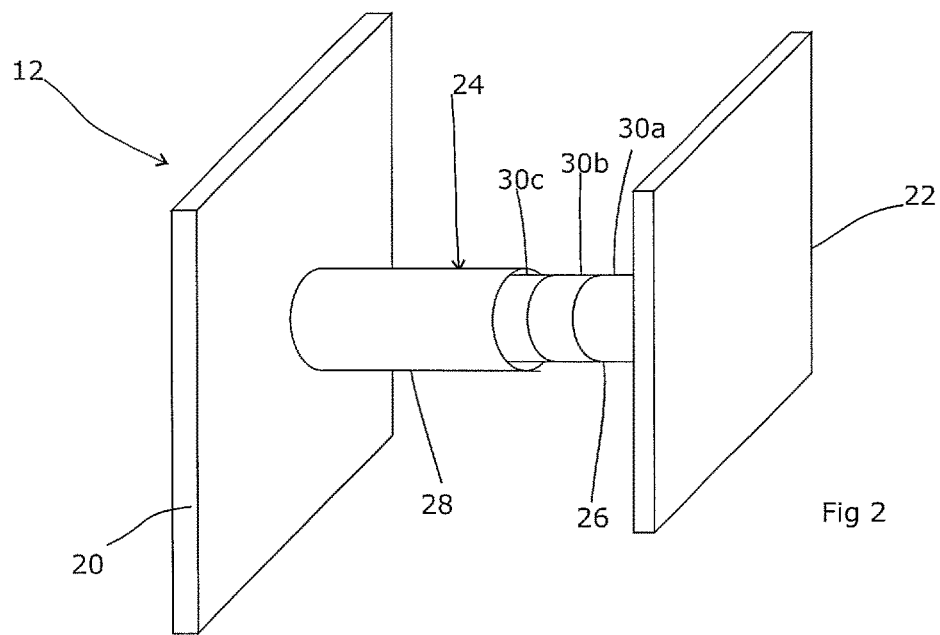
FIG. 2 shows an isometric view of the pillow selection tool.

FIGS. 2 to 4 show the pillow sizer 12 in detail. It comprises a pair of flat end plates 20, 22 between which extends a telescopic centre section 24. The end plates 20, 22 are attached on either end of the telescopic section 24, and thus move away from and toward each other as the telescopic section 24 extends and retracts.

The telescopic centre section 24 itself comprises a cylindrical inner sleeve 26 and a hollow cylindrical outer sleeve 28. The inner sleeve 26 sits within the outer sleeve 28 and can slide back and forth, with a degree of friction to allow the position of the pillow sizer 12 to be retained for a short period, to allow a reading to be taken. Thus, one end plate 20 is attached to the free end of the outer sleeve 28 whilst the other end plate 22 is attached to the free end of the inner sleeve 26.

The inner sleeve is marked on its outer cylindrical face with a series of graduations $30a$, $30b$, $30c$ (etc). Each graduation extends over a defined longitudinal length of the inner sleeve 26 and ends adjacent the next graduation. Thus, graduation $30a$ extends over a short distance of about 10 mm from (in this example) the end of the inner sleeve at the junction with the end plate 22. The next graduation $30b$ extends from the edge of the graduation $30a$ along the length of the inner sleeve for a further 10 mm or so. Graduation $30c$ extends for a further 10 mm or so, likewise. Two further graduations $30d$, $30e$ are also provided in this example, but are not visible in FIG. 2 as they are concealed within the outer sleeve 28. They are instead visible in FIG. 3 which shows a side view of the sizer 12 in its fully extended state. Generally, the graduations can be of between about 10 mm and about 25 mm in length, and need not necessarily all be equal.

The graduations $30x$ are printed on the inner sleeve 26 in different colours, preferably easily identified primary and secondary colours. This makes it a straightforward matter to view the sizer 12 after sizing and identify the size group indicated. Other visible indicia such as letters, numbers, patterns or combinations therefore could be used, however.

Thus, the sizer is capable of measuring a range of distances. The minimum distance is $C_1+C_2+S$ where $C_1$ is the thickness of the end cap 20, $C_2$ is the thickness of the end cap 22, and S is the length of the longer of the two sleeves 28. The maximum distance is $C_1+C_2+2S$, assuming that the inner sleeve 26 and outer sleeve 28 are the same length. By appropriate selection of these dimensions and appropriate placing of the graduations $30x$, the colour bands can be made to correspond to useful size ranges of pillows. The approximate dimensions which we have found to be particularly useful are as follows:

Thickness of both end caps: 4 mm
Length of outer sleeve: 80 mm
Length of inner sleeve: 100 mm
Width of graduations between 10 mm and 25 mm It will of course be desirable to adopt a standard measurement for the thickness of a pillow, which can be compared to the thickness that is identified as being suitable for the individual customer after they have been measured. What matters is not especially the thickness of the pillow when uncompressed, but the thickness of the pillow while it is supporting the user during sleep. In other words, the important dimension of the pillow is that after compression by a weight approximately equal to that of the user's head. This will be related to the uncompressed thickness of the pillow by the hardness of the pillow and by the weight of the head, with only the latter being known (approximately).

Thus, we wish to quantify the thickness of a pillow according to a scale that can be reliable and consistent. A method of doing so is to measure a linear dimension of a pillow (typically its thickness) after applying a predetermined compressive force to at least part of the pillow. The thickness of the thus compressed pillow can then be measured. The compressive force is ideally approximately the same as the weight of a typical user's head, typically between 3.5 kg and 5.5 kg. It is preferably applied between a pair of jaws, one of which can be static and one of which can be moveable (thereby to apply the force). The thickness of the compressed pillow can be measured by determining the spacing of the jaws after application of the force. A proximity sensor can be used in order to do so, if desired.

Figure 5:
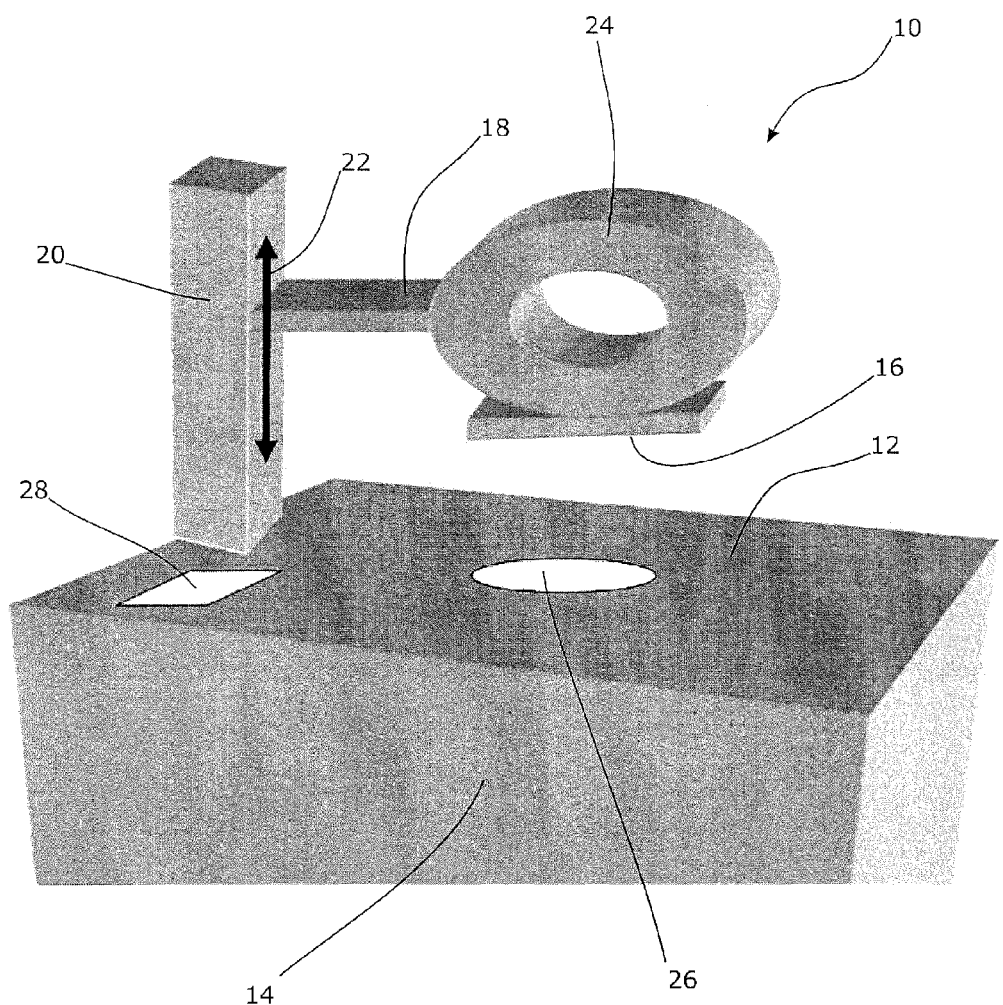
FIG. 5 shows a view of an apparatus for determining the thickness of a pillow.

FIG. 5 shows an apparatus 10 for doing so. It comprises a first planar surface 12, which is the stationary upper face of a base unit 14 that can sit on a floor or other suitable location, or can be integrated into a worktop or the like. A second planar surface 16 is provided, opposite the first planar surface 12 and between which a pillow is placeable. The second planar surface 16 is a lower face of a moveable arm 18 which is mounted on an upright 20 so that it is freely moveable toward and away from the first planar surface 12, in the direction of arrow 22. The moveable arm 18 includes a ballast weight 24 such that its total weight corresponds to the predetermined weight under which the pillow's thickness is to be measured. The ballast weight could be replaceable or supplementable with one of a range of ballast weights, to reflect the approximate head weight of a particular user. The weight could be chosen based on a customer's measured dimension, as physically larger users tend to have heavier heads.

Thus, the moveable arm 18 is lifted, the pillow is placed beneath it, and the arm 18 is then released or lowered onto the pillow.

Alternatively, a drive means and a force sensor could be integrated into the upright 20. The drive means would move the arm 18 up and down, and the force sensor would control the drive means under a negative feedback loop such that once a predetermined force is being exerted, the drive means would stop at that point. This would obviate the need for the fixed weight, but at the cost of additional complexity.

A proximity measuring device 26 is built into base unit 14. This detects the distance between the first and second planar surfaces 12, 16. It can be a laser, optical, contact type, ultra sonic, eddy current, Hall effect or an X-ray device, or any other like device. This then produces a signal indicative of the distance, which is displayed as a digital readout on a display 28. The first planar surface 12, under which the proximity sensor is attached, could be a rigid flat surface or a deformable surface with compressive properties similar to a mattress, to represent a pillow on a bed. Indeed, the first planar surface 12 could be a section of mattress.

Thus, the pillow to be measured is placed on the bench directly over the proximity measuring device. The weight with the upper sensor plate attached is lowered onto the pillow. When the weight has rested on the pillow for a set period of time the reading of the compressed pillow height can be gleaned from the digital read out.

In this way, pillows could be sized in advance of sale and packaged (or otherwise marked) with an indicia showing the size range into which they fall. This could then be correlated with a customer's measured dimension. Alternatively, a customer could be measured and then device then used in situ in the retail establishment to test one or more candidate pillows in order to identify one that is suitable, adjusting the ballast weight as required (if desired).

It will of course be understood that many variations may be made to the above-described embodiment without departing from the scope of the present invention.

The invention claimed is:

1. A method of selecting a pillow for a user, comprising the steps of:
   locating the user with an outside of a shoulder thereof abutting an upright flat rigid surface,
   orienting the user substantially transverse to the surface,
   providing an apparatus configured for measuring a deltoid temporal distance and comprising a telescopic centre section having a series of graduations marked thereon and located between a pair of movably biased opposing end plates;
   positioning the apparatus within a space between the surface and a proximate side of the user's head;
   extending or retracting the centre section and positioning the end plates for measuring the spacing between the surface and a proximate side of the user's head, and
   selecting at least one pillow from a group of pillows, based on the measured spacing.

2. The method according to claim 1 in which the upright rigid surface is a wall.

3. The method according to claim 1 in which the group of pillows is divided into a plurality of sub-groups, each sub-group containing a plurality of pillows with substantially like thickness.

4. The method according to claim 3 in which each pillow carries a visible indicia indicating the sub-group to which it belongs.

5. The method according to claim 1 in which the spacing is measured by a time-of-flight device.

6. The method according to claim 1 in which the spacing is measured using the apparatus comprising the telescopic centre section located between the pair of opposing end plates, the centre section having a visible indicia indicative of a distance between the end plates.

7. The method according to claim 1 in which the spacing is measured using the apparatus wherein the end plates can move away from and toward each other as the telescopic centre section extends and retracts and wherein the centre section comprises a series of graduations marked on its outer face to indicate a distance between the end plates.

8. The method according to claim 7, and wherein one end plate has a dimension transverse to the centre section that is greater than that of the other end plate, the dimension providing a flat rigid surface configured to abut against an outside of a shoulder muscle of a user for measuring the deltoid temporal distance.

* * * * *